United States Patent [19]
Pohl et al.

[11] Patent Number: 5,630,815
[45] Date of Patent: May 20, 1997

[54] EXTERNAL FIXATOR FOR MILITARY USE

[76] Inventors: Anthony P. Pohl, 8 Caralue Road, Marino, South Australia, Australia, 5049; Bruce H. Ide, 7 Orchard Court, Newton, South Australia, Australia, 5074

[21] Appl. No.: 510,345

[22] Filed: Aug. 2, 1995

[30] Foreign Application Priority Data

Aug. 5, 1994 [AU] Australia .................. PM7311

[51] Int. Cl.[6] ........................... A61B 17/60
[52] U.S. Cl. ................... 606/59; 606/54; 7/138
[58] Field of Search ............... 606/53, 54, 57, 606/58, 59, 55, 80, 1; 7/138, 140, 142, 158

[56] References Cited

U.S. PATENT DOCUMENTS

| | | | |
|---|---|---|---|
| 4,229,999 | 10/1980 | Rottigni | 7/138 |
| 4,549,324 | 10/1985 | Liou | 7/142 |
| 4,791,690 | 12/1988 | Kuang-Wu | 7/138 |
| 4,960,016 | 10/1990 | Seals | 7/138 |
| 5,086,674 | 2/1992 | Her | 7/138 |
| 5,313,680 | 5/1994 | Ringler | 7/138 |
| 5,454,810 | 10/1995 | Pohl et al. | 606/54 |

*Primary Examiner*—Michael Buiz
*Assistant Examiner*—Patrick W. Rasche
*Attorney, Agent, or Firm*—Townsend and Townsend and Crew LLP

[57] ABSTRACT

The invention provides an improved external fixation device which is designed for use in the treatment of bone fractures in a military setting, and comprises a main hollow housing (11) having opposite open ends, first and second end closure members (12, 13) removably attached to the opposite ends of the housing, the member (12) comprising a drill handle forming element (26) while the member (13) comprises a chuck-forming element (31), the end members (12, 13) when detached from the housing (11) being adapted for gripping engagement within respective clamp holders (14, 15) so as to form a hand tool assembly which can operate as a brace-and-bit. A bit element (40) is releasably locked in the socket (38) of the chuck element (31). A holder unit (33) is housed within the interior of the housing (11) and serves to store the ancillary equipment (40, 41, 42) within the housing during transport of the device.

15 Claims, 4 Drawing Sheets

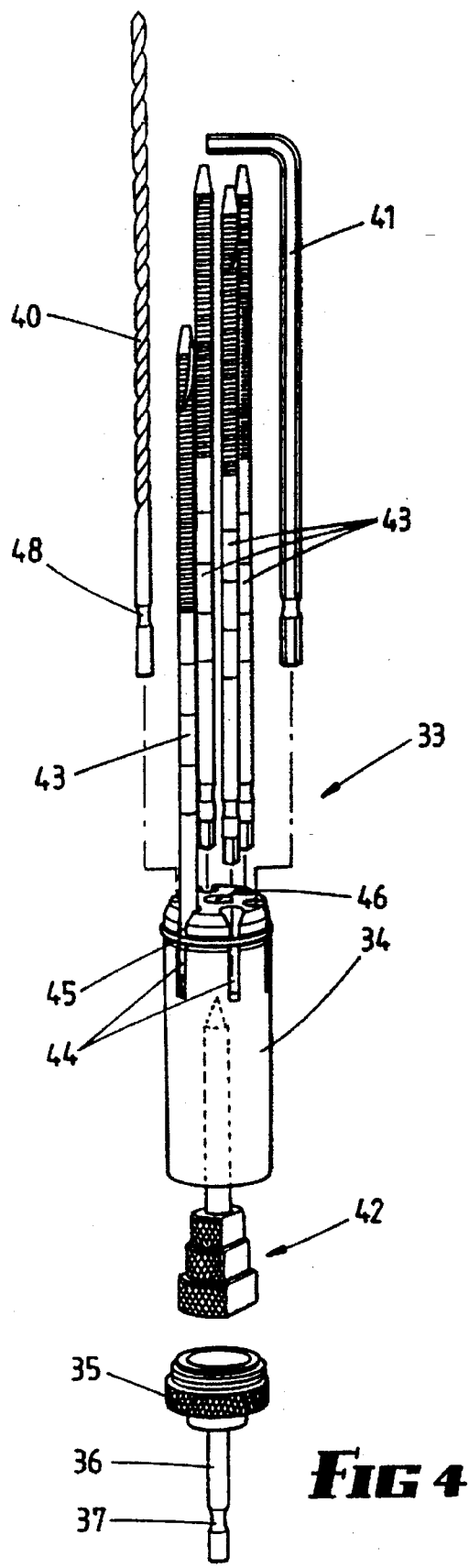
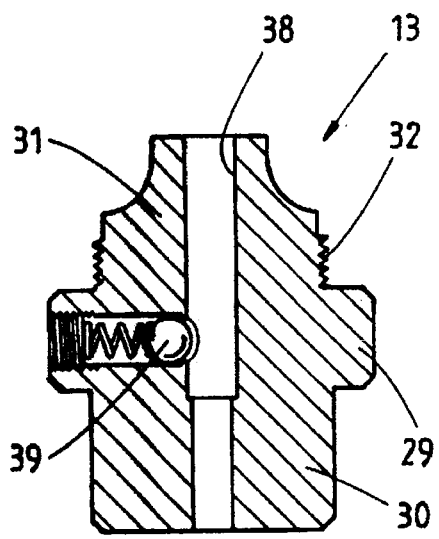
FIG 5
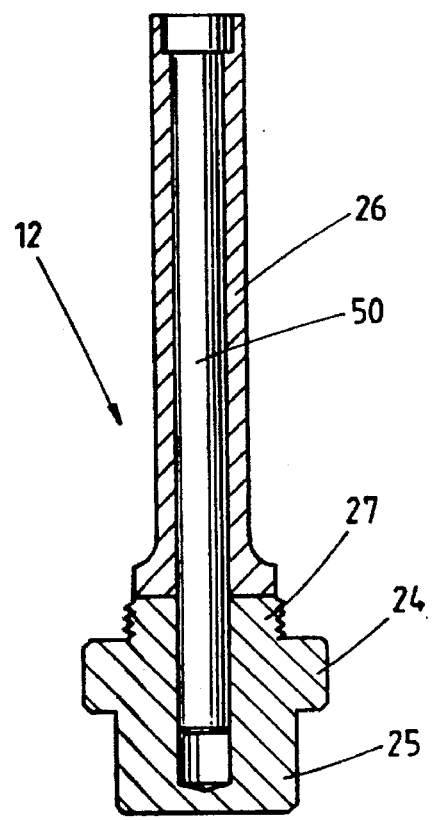
FIG 6
FIG 4

EXTERNAL FIXATOR FOR MILITARY USE

This invention relates to an external fixation device used in the treatment of bone fractures in a military setting, and more specifically to an improved unilateral (one-sided), single frame fixation device which, in one mode of use, can be configured to form a bit and brace for the purpose of inserting threaded bone fixator pins into the fractured bone.

The primary purpose of an external fixator for military use is to hold together, by means of pins, the fragments or sections of a fractured bone while the patient is being safely evacuated from the hostile zone and in turn permit the healing process to progress while allowing the patient to retain mobility of neighbouring joints. To perform this task, the fixator must be sufficiently rigid or stiff to support the loads imposed on it without allowing excessive movement of the fracture site.

The use of external fixation devices is an established and recommended form of treatment in many forms of limb injury and many different fixation devices have been designed and are known to the applicants. Some of these fixation devices have been intended for military use. In this regard, reference is made to the "Ultra-X" fixator (Howmedica) and the "Hammer" fixator (Biomet). It is considered however that known military fixators do not provide the degree of rigidity required for patient transport or optimal bone healing and do not meet requirements of size and weight required by the military—it being appreciated that such devices are carried by army personnel in the field and hence should be compact and of lightweight.

A significant drawback therefore associated with known external fixation devices has been their bulkiness and weight. In an effort to decrease size and weight, fixators have been designed with smaller diameter support bars or rods and have avoided the use of heavy metallic materials; however, such units are less rigid and do not provide the necessary level of rigidity required for military use.

Another drawback associated with known devices is that they require an independent drill to pre-drill or insert the threaded pins into the bone. Air driven (pneumatic) drills are commonly used, but are not stand-alone devices, which preclude their ready use for military purposes in the field. Portable battery powered electric drills are also commonly used, but these must be fully charged and may fail if exposed to sandy conditions or immersed in water.

It is also known for external fixation devices designed for military use to have an accompanying brace-and-bit as a separate item, but this inclusion increases the size and weight of the overall fixator package.

Ancillary equipment including scalpels, trochar-cannulae sets for the protection of soft tissues, and jigs to ensure correct pin positioning are required for safe and correct application of external fixation devices. Such equipment is normally included in supplementary packs with the external fixation devices resulting in an increase in the size and weight of the packaged fixator unit.

It is the main object of the present invention therefore to provide an improved unilateral external fixation device for military use having component parts which can be interconnected in a manner so that the device can act as a brace-and-bit to assist in the insertion of the fixator pins, and which thereby avoids the need for an operator to have to separately carry a drilling tool as is presently the case with known military fixator units.

It is another object of the present invention to provide an improved external fixation device which, along with the ancillary equipment, eg scalpels, trochar-cannulae sets and fixation pins, can be conveniently and economically packaged and transported.

It is yet another object of the present invention to provide an improved military external fixation device which can be transported and used in the field with minimal additional equipment.

It is a still further object of the present invention to provide an improved unilateral external fixation device which allows its fixator body to be readily coupled to the fixator body of a similar fixation device so that two or more fixator bodies can be coupled together to form a frame of adequate length for the fixation of multiple unilateral compound limb fractures or injured joints. This is a feature which may be required in order to externally fix multiple fractures and injured joints between the foot and the pelvis in a lower limb.

It is a still further object of the present invention to provide an improved external fixation device which is designed so that it can be readily converted from a rigid military fixator to one which permits dynamisation.

Broadly according to this invention therefore, an external fixation device for military use comprises:

an elongate cylindrical hollow fixator housing having a bore extending therethrough, first and second end closure members removably attached to the opposite open ends of said fixator housing for closing off same, said first closure member comprising a chuck-forming element, said second closure member comprising a drill handle-forming element, said chuck-forming element and said drill handle-forming element being housed within the bore of the fixator housing, when the closure members are attached to their respective ends, a pair of pin clamp assemblies adjustably carried on the fixator housing for selective positioning along the length thereof, each said pin clamp assembly comprising a pin clamp holder supported by the fixator housing and projecting laterally to one side thereof, said first and second end closure members, when detached from the ends of the fixator housing, being adapted for gripping engagement respectively within said clamp holders, with the drill handle-forming member and the chuck-forming element extending away from their associated clamp holders in opposite directions to thereby form, with the hollow fixator housing, a hand tool assembly which can be operated as a brace-and-bit, with a bit element being releasably retained within a socket of said chuck-forming element.

Desirably, the bore is sized to permit storage of ancillary equipment which would normally comprise a scalpel, a drill bit, a trochar-cannulae set, an Allen key and bone fixation pins.

The bit element can be a fixator pin of the self-drilling type.

Each of the clamp holders when the device is operating as a fixation device, releasably supports a respective pin clamp. Each clamp has releasably secured therein one or more bone fixator pins.

Preferably each said end closure member, at one end thereof, is formed with a cylindrical boss or skirt which is gripped by its associated clamp holder when the fixator is assembled as a brace-and-bit.

Preferably each of the first and second end closure members is threadably connected to the fixator housing, with the housing having internally threaded portions at its opposite ends.

Preferably the opposite ends of the bore of the fixator housing are adapted so that the end of one fixator housing can be coupled to an end of another like fixator housing so as to co-axially join two or more fixator housings together. An adaptor having male threaded ends may be used for this purpose.

Desirably, the ancillary equipment is stored within the interior of the fixator housing by means of a holder unit which removably locates within the housing. The holder unit is coupled to the chuck-forming element by means of a rigid connector rod which releasably snap-fittingly connects to the socket of the chuck-forming element. With connector rod thus engaged, the holder unit is fixed with respect to the housing and ensures that the ancillary equipment is safely and securely stored in the interior of the housing.

Preferably, the holder unit comprises a hollow cylindrical pod, one end of which is open, and an end closure cap which is screw-threaded to the open end of the pod, the connector rod being integral with the end closure cap.

With this invention therefore, the hollow fixator body can be used to store the ancillary equipment, and there is no need for an operator to have access to a separate drilling tool due to the fact that the fixator body together with the end closure members and the pin clamp holders, enable the fixation device to be converted to a brace. This allows the fixator unit to be packaged in a small volume package with a significant reduction in weight in comparison to known units.

In order to further explain the present invention, an embodiment is described hereunder in some further detail with reference to and as illustrated in the accompanying drawings wherein:

FIG. 4 is an exploded perspective view of the holder unit which is stored within the main body and the ancillary equipment carried by the holder;

FIG. 5 is a sectioned view of the chuck-forming element; whilst

FIG. 6 is a sectioned view of the handle-forming element.

Figure 1:
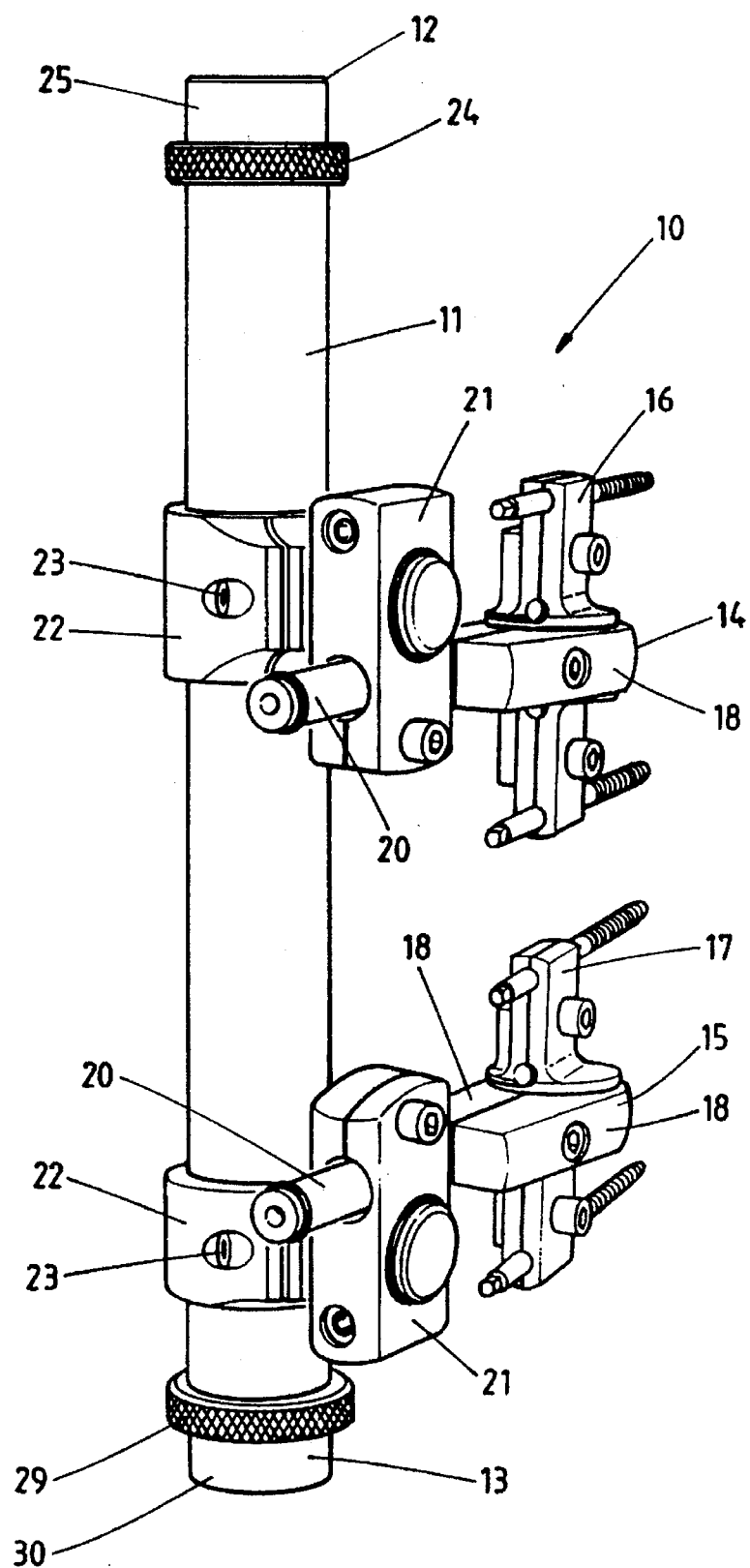
FIG. 1 is a perspective view of a military external fixator unit according to a preferred embodiment of the invention.

In this embodiment, an external fixation device 10 comprises an elongate hollow housing or main support body 11, end closure members 12, 13, a pair of pin clamp holders 14, 15 adjustably supported by the fixator body 11, and a pair of pin clamps 16, 17 carried by said clamp holders 14, 15 respectively.

The construction and operation of the pin clamp holders, their manner of attachment to the fixator body 11, and also the pin clamps 16, 17 are essentially the same as that which has been described in our earlier Australian Patent Specification No 648542, the contents of which are incorporated herein by reference.

Specifically each clamp holder 14, 15 comprises a pair of semicircular lugs 18 which co-operate together to form a circular opening for clampingly receiving the pin clamps 16, 17, the semicircular lugs 18 joining to a shaft 20 which is rotatably received in a through-opening formed in a swivel connector block 21 which in turn is mounted to a connector collar or bracket 22 which encircles the fixator body 11 and clamped thereonto by screws 23. With the connector bracket 22 untightened, the clamp holder 14, 15 is able to be adjustably positioned along the length of the fixator body 11. In addition, the clamp holders 14, 15 are able to rotate about the axes of their shafts 20. These features are described in detail in the aforesaid Australian patent specification.

Figure 2:
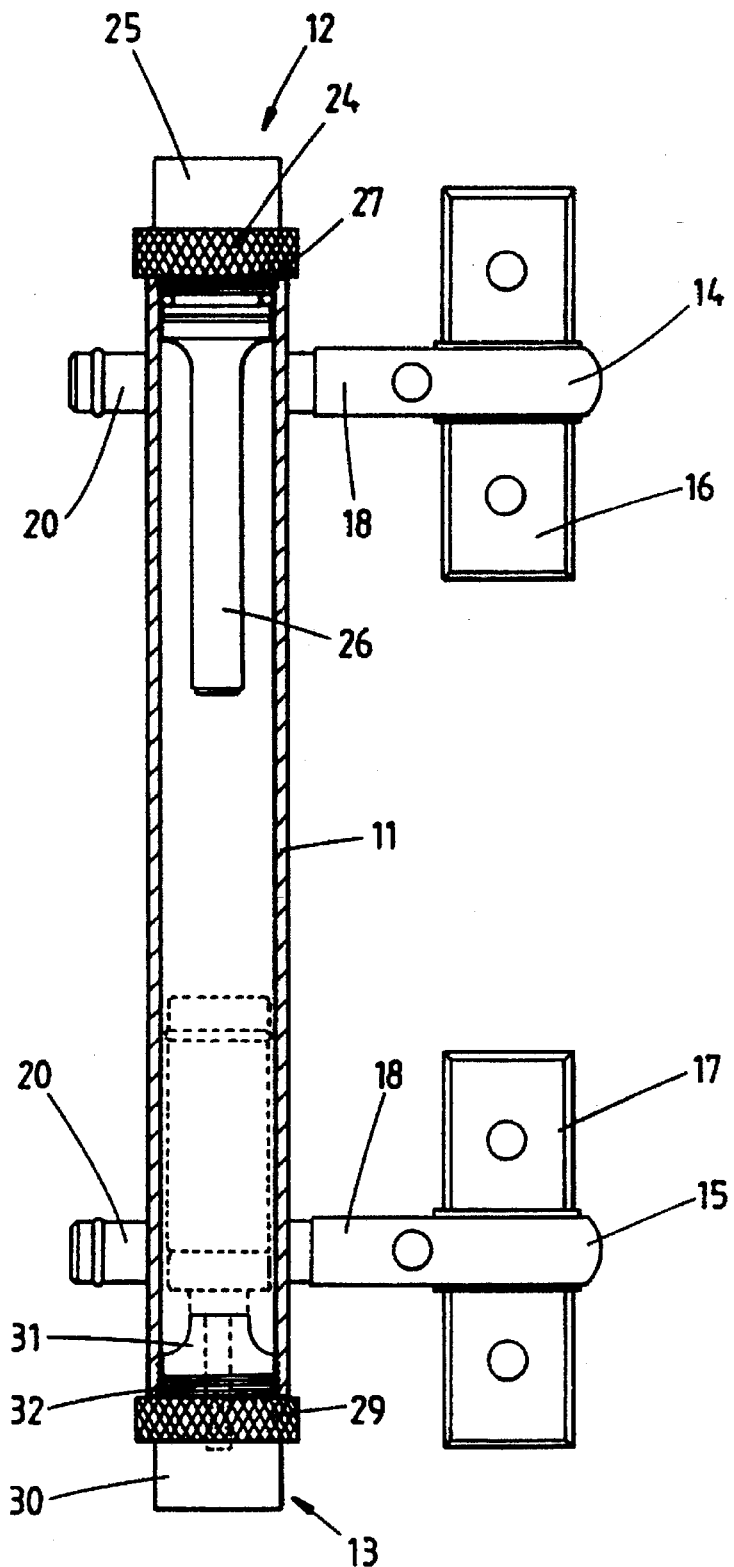
FIG. 2 is a part longitudinal section of the fixator unit shown in FIG. 1.

Referring to FIG. 2 of the drawings, the end closure member 12 comprises an annular flange 24 which has a knurled outer peripheral surface, a cylindrical end portion 25 projecting to one side of the flange 24 and an elongate rod or shaft 26 which projects to the other side of the flange 24 centrally thereof, the rod 26 connecting to an enlarged externally threaded body portion 27 which in turn connects to the flange 24. When the fixator unit is in its transport mode of use, the member 12 is connected to the end of the fixator body 11 by screwing the body portion 27 into the internally threaded end of the bore of the fixator body 11.

The end closure member 13 similarly comprises an annular flange 29 having a knurled outer peripheral surface, a cylindrical end portion 30 projecting to one side of the flange 29 and a centrally located chuck-forming assembly 31 on the other side of the flange 29, the inner end of the chuck-forming assembly 31 connecting to an externally threaded boss portion 32 which has an outer diameter approximately equal to the diameter of the bore of the body 11. When the fixator is in its transport mode of use, the closure member 13 is fitted to the other end of the body 11 by screwing the body portion 32 into the bore of the body 11.

In this embodiment, each of the body portions 27, 32 is provided with an annular groove in which is located an O-ring for sealingly engaging the bore surface of the body 11. This prevents the ingress of any contaminants or foreign particles into the interior of the fixator body 11.

As shown in FIG. 2, the space between the facing ends of the chuck-forming member 31 and the rod or shaft 26 permits certain ancillary equipment to be stored therein. The unit is thus self-contained and there is no need for any additional equipment to be carried. In this embodiment, there is provided a holder assembly 33 (refer FIG. 4) which comprises a hollow cylindrical pod 34 and an end closure cap 35 which threadably connects to the pod 34. The cap 35 has integrally formed therewith an elongate stem 36 which releasably connects to the chuck 31 by means of a snap-fit. The stem 36 has a locking groove 37 which, when the stem is inserted into the passage 38 of the chuck 31, co-operates with a spring-loaded ball detent 39 mounted in the chuck 31, in order to releasably lock the stem 36 to the chuck 31. With the stem 36 thus locked, the pod 34 is fixedly held in place within the housing.

The ancillary equipment is shown in FIG. 4 and will normally comprise an Allen key 41, a trochar-cannulae set 42, a drill bit 40, a plurality of bone fixator pins 43 and a scalpel (not shown). The drill bit 40, pins 43 and key 41 are located in external grooves 44 spaced around the circumference of the pod 34 and retained in place by circlips 45, while the trochar-cannulae set 42 is housed in the interior of the pod 34 with its spiked end being arranged in use, to project through the small diameter passage 46 extending axially of the pod 34.

Figure 3:
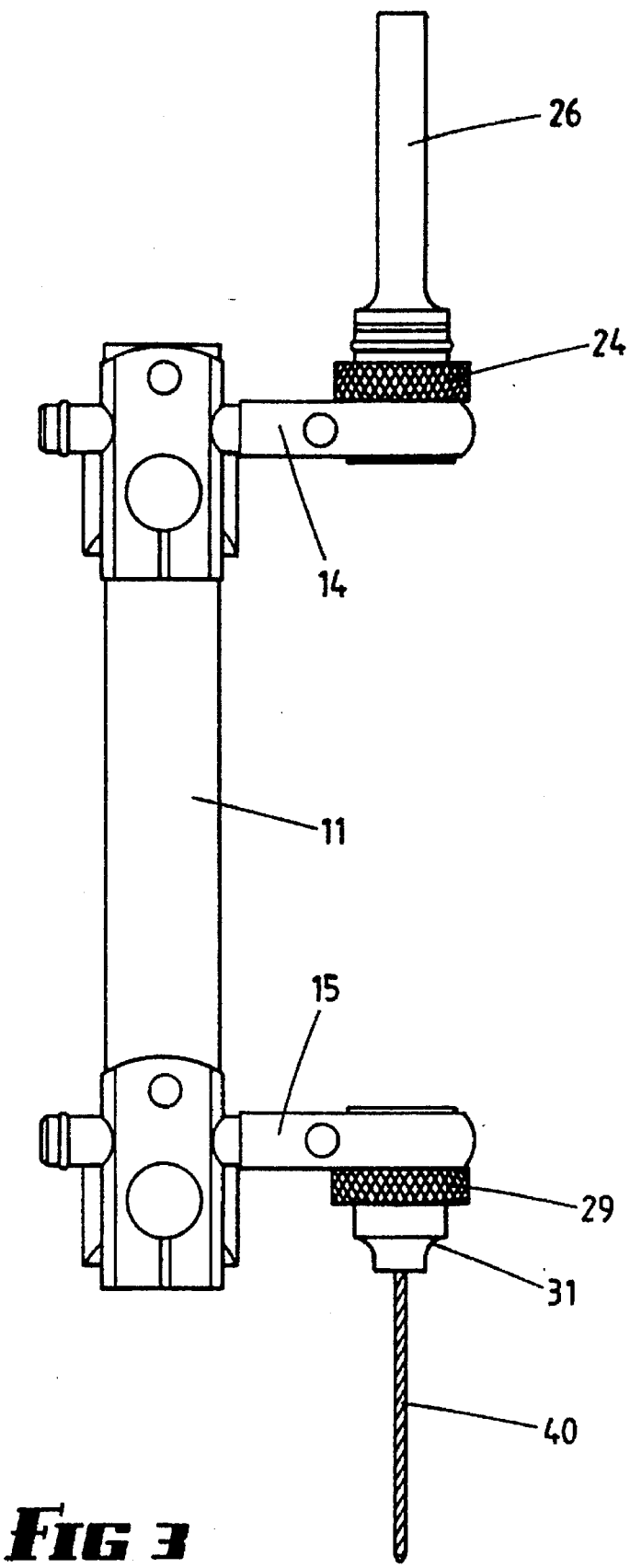
FIG. 3 is a view similar to FIG. 1 showing the fixator unit converted to its mode of use as a brace.

Referring to FIG. 3 of the drawings, the fixator unit is shown in its mode of use as a brace-and-bit, with the pin clamps 16, 17 having been removed from their clamp holders 14, 15.

Each of the end closure members 12, 13 is unscrewed from its end on the fixator body 11 and is clamped in its clamp holder 14, 15 by inserting end portion 25, 30 into the circular opening formed by the lugs 18 of the clamp holder. The clamp holders are suitably tightened by means of the Allen key 41 which is provided as part of the ancillary equipment.

The drill bit 40 is snap-fittingly inserted into the socket 38 of the chuck element 31. The mounting end of the bit 40 is provided with a locking groove 48 which together with the detent ball 39 of the chuck 31 serve to lock the bit 40 in the socket 38 while drilling is carried out. It will of course be appreciated that the pins 43 which can be self-drilling and self-tapping, may be used as a bit instead of the drill bit 40.

The fixator unit is now ready for use as a brace-and-bit for inserting the pins 43 into the fractured bone.

Referring to FIG. 6 of the drawings, the handle 26 is rotatably carried on a shaft 50 so that it can freely rotate during drilling.

The clamping screws on the fixator unit can also be loosened or tightened by means of a straight handled wrench, or a torque wrench.

Desirably, the pin clamps 16, 17, when removed from their clamp holders, are used as a jig for accurately positioning the fixator pins 43 as they are being drilled into the fractured bone. This is achieved by inserting the ends of the pins through open-ended pin locating passageways which extend transversely through the clamps 16, 17.

If necessary, the fixator body 11 can be readily replaced by a dynamising fixator body of the kind described and illustrated in Australian patent 648542 in order to convert it from a rigid fixator to a dynamising fixator. This can be done by simply detaching the connector brackets 22 from the fixator body 11 and inserting a dynamising fixator body which has the same outer diameter as that of the body 11.

In an alternative embodiment, the chuck-forming element 31 may comprise a set of radially expansible jaws which are retained by clamping nuts. With the nuts loosened the end of the bit 40 can be inserted into the socket and held therein upon tightening of the nuts.

A brief consideration of the above described embodiment will indicate that the invention provides an extremely simple external fixation device suitable for military use which is of lightweight construction, provides its own storage space for the ancillary equipment and is able to be readily converted into a hand drill in the form of a brace which can then be used to insert the bone fixation pins.

What we claim is:

1. An external fixation device for military use comprising:

an elongate hollow fixator housing having a central bore extending therethrough, first and second end closure members removably attached to and closing off opposite open ends of said fixator housing, said first closure member comprising a chuck-forming element, said second closure member comprising a drill handle- forming element, said chuck-forming element and said drill handle forming element, when the device is in a transport mode of use, being housed within the bore of said fixator housing, a pair of pin clamp assemblies adjustably carried on the fixator housing for selective positioning along the length thereof, each said pin clamp assembly comprising a pin clamp holder supported by the fixator housing and projecting laterally to one side thereof, said first and second end closure members, when detached from the ends of the fixator body, being adapted for gripping engagement respectively within said clamp holders, with the drill handle-forming member and the chuck-forming element extending away from their associated clamp holders in opposite directions to thereby form, with the hollow fixator housing, a hand tool assembly which can be operated as a brace-and-bit, with a bit element being releasably retained within a socket of said chuck-forming element.

2. An external fixation device according to claim 1 wherein said bit element is a bone fixator pin.

3. An external fixation device according to claim 2 wherein said fixator pin is of the self-drilling and self-tapping type.

4. An external fixation device according to claim 1 wherein said chuck-forming element comprises a spring-loaded detent which is arranged to lockingly engage within a locking groove formed adjacent one end of the bit element, when the bit element is inserted into the socket.

5. An external fixation device according to claim 1 wherein each of said first and second end closure members has a threaded body portion which threadably engages with a respective end portion of the fixator housing.

6. An external fixation device according to claim 5 wherein each of said first and second end closure members is formed with a cylindrical boss or skirt arranged to clampingly engage within a respective one of said clamp holders when the fixator device is assembled as a brace-and-bit.

7. An external fixation device according to claim 1 wherein said fixator housing is cylindrically shaped.

8. An external fixation device according to claim 1 wherein each of said first and second closure members is formed with a circular annular flange intermediate the ends thereof, the outer diameter of the flange being greater than the outer diameter of the fixator housing, said flange being adapted to abut against a respective end of said housing when the closure member is connected thereto.

9. An external fixation device according to claim 1 wherein said handle-forming element comprises an elongate handle member which is rotatably mounted on said second closure member and is co-axial therewith.

10. An external fixation device according to claim 1 further comprising a holder unit removably housed within the bore of the housing and adapted for the storage of ancillary equipment for the fixation device internally of the housing.

11. An external fixation device according to claim 10 wherein said holder unit comprises an open-ended hollow container sized to slidably fit within said bore and locate between the inner ends of said end closure members, and an end closure cap removably attached to the open end of the container.

12. An external fixation device according to claim 11 wherein said end cap is provided with an integrally formed co-axial connecting stem extending outwardly therefrom and adapted to lockingly engage within the socket of said chuck-forming element to thereby hold the holder unit in fixed relation with the housing.

13. An external fixation device according to claim 12 wherein said connecting stem is adapted to engage with the socket with a snap-fit.

14. An external fixation device which is positionable in a first mode wherein the device is adapted for connection to a bone for rigid fixation thereof and in a second mode wherein the device is configured as a brace-and-bit, said device including a tubular housing with a chuck-forming member and a handle forming member carried therein, said handle forming member and said chuck-forming member, when said device is in said second mode, being connected to the housing at opposite ends thereof and being laterally offset from said housing.

15. The device of claim 14 wherein in said first mode, said chuck-forming member and said handle forming member are carried within said tubular housing.

* * * * *